(12) United States Patent
Jensen et al.

(10) Patent No.: US 9,237,243 B2
(45) Date of Patent: Jan. 12, 2016

(54) EMERGENCY INCIDENT CATEGORIZATION AND ALERTING

(71) Applicants: Anne Marie Jensen, Carlsbad, CA (US); Winston Yu, San Diego, CA (US)

(72) Inventors: Anne Marie Jensen, Carlsbad, CA (US); Winston Yu, San Diego, CA (US)

( * ) Notice: Subject to any disclaimer, the term of this patent is extended or adjusted under 35 U.S.C. 154(b) by 0 days.

(21) Appl. No.: 14/497,120

(22) Filed: Sep. 25, 2014

(65) Prior Publication Data

US 2015/0092928 A1    Apr. 2, 2015

Related U.S. Application Data

(60) Provisional application No. 61/883,390, filed on Sep. 27, 2013.

(51) Int. Cl.
| | |
|---|---|
| H04M 11/00 | (2006.01) |
| H04M 11/04 | (2006.01) |
| G06F 17/30 | (2006.01) |
| G06Q 50/26 | (2012.01) |
| G06F 19/00 | (2011.01) |
| G06Q 10/06 | (2012.01) |

(52) U.S. Cl.
CPC ........... *H04M 11/04* (2013.01); *G06F 17/3071* (2013.01); *G06F 19/322* (2013.01); *G06F 19/3418* (2013.01); *G06F 19/3443* (2013.01); *G06Q 10/06311* (2013.01); *G06Q 50/265* (2013.01); *H04M 2242/04* (2013.01)

(58) Field of Classification Search
CPC ............ H04M 11/04; H04M 2242/04; H04M 3/5116; G06Q 50/22
USPC ........................................................ 379/45
See application file for complete search history.

(56) References Cited

U.S. PATENT DOCUMENTS

| | | | |
|---|---|---|---|
| 5,978,671 A | 11/1999 | Foladare et al. | |
| 6,600,812 B1 * | 7/2003 | Gentillin et al. ................ | 379/45 |
| 7,177,623 B2 | 2/2007 | Baldwin | |
| 7,764,945 B2 | 7/2010 | Polk et al. | |
| 7,978,826 B2 | 7/2011 | Salafia | |
| 8,068,587 B2 | 11/2011 | Geldenbott et al. | |
| 8,165,560 B2 * | 4/2012 | Stenquist .................. | 455/404.1 |
| 8,447,025 B2 | 5/2013 | Shaffer et al. | |
| 8,976,939 B1 * | 3/2015 | Hamilton et al. ............... | 379/45 |

(Continued)

FOREIGN PATENT DOCUMENTS

WO    WO 2007/121570    11/2007

OTHER PUBLICATIONS

Busch, Jason. How Using Existing Data is Changing the Way EMS Treats Vulnerable Populations. EMS World. Feb. 1, 2014. http://www.emsworld.com/article/11291709/ems-data-use-changing-the-way-we-serve-vulnerable-populations. Accessed: Oct. 24, 2014.

(Continued)

*Primary Examiner* — Stella L Woo
(74) *Attorney, Agent, or Firm* — Kobbe Martens Olson & Bear LLP

(57) ABSTRACT

A method and system for identifying and addressing community issues that burden the emergency response system, the method including receiving an electronic report for an incident, matching a person or location identifier from the electronic report with patient-centric data from a database, and providing an alert to a specialized caregiver if the identity or incident matches a list of frequent or high priority emergency service users.

18 Claims, 18 Drawing Sheets

(56) References Cited

U.S. PATENT DOCUMENTS

| | | |
|---|---|---|
| 2002/0106059 A1* | 8/2002 | Kroll et al. .................... 379/45 |
| 2005/0131740 A1* | 6/2005 | Massenzio et al. ............. 705/2 |
| 2009/0214000 A1* | 8/2009 | Patel et al. .................... 379/45 |
| 2010/0166154 A1 | 7/2010 | Peters |
| 2011/0212703 A1 | 9/2011 | Gardner et al. |
| 2012/0295573 A1 | 11/2012 | Park et al. |
| 2013/0122851 A1 | 5/2013 | Michaelis et al. |
| 2013/0143517 A1 | 6/2013 | Mitchell et al. |
| 2014/0072111 A1* | 3/2014 | Klaban ......................... 379/45 |

OTHER PUBLICATIONS

Data-Driven System Helps Emergency Medical Services Identify Frequent Callers and Connect Them to Community Services, Reducing Transports and Costs. U.S. Department of Health & Human Services. Agency for Healthcare Research and Quality (AHRQ). https://innovations.ahrq.gov/profiles/data-driven-system-helps-emergency-medical-services-identify-frequent-callers-and-connect . Accessed: Oct. 24, 2014.

First Watch. What We Do. Turning Raw Data into Meaningful Information. http://www.firstwatch.net/what-we-do/. Accessed: Oct. 23, 2014.

Jensen et al. San Diego's eRAP System Redirects Frequent Flyers. Journal of Emergency Medical Services. Technology. Jan. 2013 Issue. http://www.jems.com/article/technology/san-diego-s-erap-system-redirects-freque. Accessed Oct. 24, 2014.

Kizer et al. Community Paramedicine: A Promising Model for Integrating Emergency and Primary Care. UC Davis Institute for Population Health Improvement. Jul. 2013. pp. 1-24.

Mintz-Habib, M.1; Rawat, A.1; Schulzrinne, H.1; Wu, X.1. A VoIP emergency services architecture and prototype. Author Affiliation(s): Dept. of Comput. Sci., Columbia Univ., New York, NY, USA. Book Title: Proceedings. 14$^{th}$ International Conference on Computer Communications and Networks (IEEE Cat. No. 05EX1184). Inclusive Page Nos. 523-8. Publisher: IEEE , Piscataway, NJ; Country of Publication: USA. Publication Date: 2005. Conference Title: Proceedings. 14th International Conference on Computer Communications and Networks. Conference Date: Oct. 17-19, 2005. Conference Location: San Diego, CA, USA. Conference Sponsor: IEEE IEEE Commun. Soc. (Tech. Cosponsor) IBM Nokia. Editor(s): Thuel, S.R.; Yang, Y.; Park, E.K. ISBN: 0-7803-9428-3.

Reducing Repeat 911 Callers. A pilot program that saved the Baltimore City Fire Department money and increased their efficiency has become a permanent fixture. BY: Caroline Cournoyer, Apr. 28, 2011. Source: http://www.governing.com/idea-center/Reducing-Repeat-911-Callers.html. Accessed: Oct. 24, 2014.

* cited by examiner

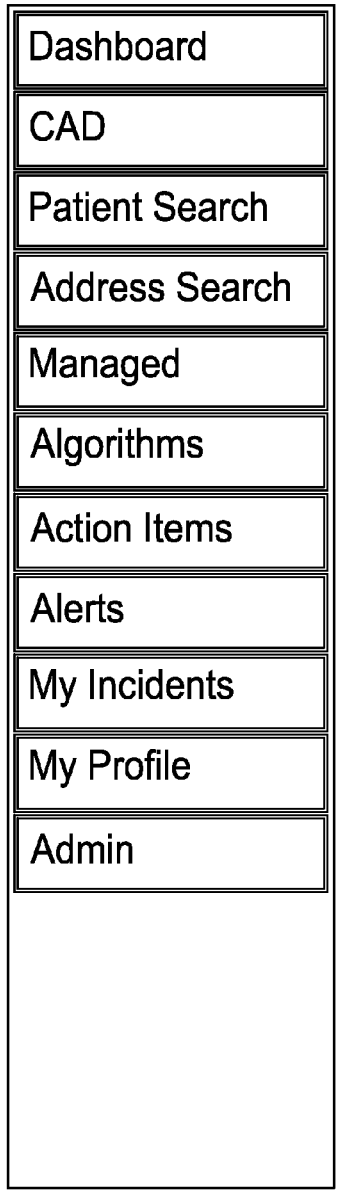

Low-level patient match threshold:
◎ Driver's License, DOB, Short last name, sex
◎ SSN, DOB, Short last name, sex
◎ Driver's License, DOB, last name, Short first name
◎ SSN, DOB, last name, Short first name
◎ Driver's License, DOB, first name, short last name
◎ SSN, DOB, first name, short last name
◎ DOB, last name, short first name, sex and zip
◎ DOB, last name, short first name, sex
◎ Driver's License, last name, first name, sex
◎ SSN, dob, address
◎ SSN, last name, first name, sex
◎ SSN, last name, first name
◎ SSN, sound last name, sound first name
◉ SSN, DOB, sex
◎ DOB, last name, sound first name, sex
◎ DOB, sound last name, first name, sex
◎ DOB, last name, first name
◎ DOB, sound last name, sound first name, sex
◎ DOB, sound last name, sound first name
◎ Last name, first name, address
◎ Sound last name, sound first, address
◎ Short SSN, DOB, short last name, sex
◎ Exact name, SIP list, ETOH-based incident
◎ Sound name, SIP list, ETOH-based incident

| secure.infotechsm.com/agencytest/ | | | | Google | |
|---|---|---|---|---|---|
| INFOTECH *AGENCY PORTAL* | | | Dashboard | | Welcome Arnie! [ Log Out ] |

| Dashboard | Frequent Homeless Users | | | | Return top 10 ▾ | ☑ Include Records on Watchlist |
|---|---|---|---|---|---|---|
| CAD | Last Week | Last 2 Weeks | Last Month | Last 6 Months | Last Year | |
| Patient Search | (3) | (6) | (9) | (57) | (99) | |
| Managed | (3) | (5) | (7) | (33) | (63) | |
| Algorithms | (3) | (4) | (7) | (33) | (58) | |
| Action Items | (2) | (4) | (6) | (29) | (48) | |
| My Profile | (2) | (3) | (5) | (27) | (47) | |
| Admin | (2) | (3) | (5) | (26) | (43) | |
| | (2) | (3) | (4) | (25) | (35) | |
| | (2) | (3) | (4) | (24) | (34) | |
| | (2) | (3) | (4) | (20) | (33) | |
| | (2) | (3) | (4) | (20) | (32) | |

| | Frequent Behavioral/Psychiatric Users | | | | Return top 10 ▾ | ☑ Include Records on Watchlist |
|---|---|---|---|---|---|---|
| | Last Week | Last 2 Weeks | Last Month | Last 6 Months | Last Year | |
| | (5) | (14) | (15) | (75) | (147) | |
| | (3) | (6) | (9) | (57) | (99) | |
| | (3) | (5) | (7) | (33) | (63) | |
| | (3) | (4) | (7) | (33) | (58) | |
| | (2) | (4) | (6) | (29) | (48) | |
| | (2) | (4) | (5) | (28) | (47) | |
| | (2) | (3) | (5) | (27) | (45) | |
| | (2) | (3) | (5) | (26) | (42) | |
| | (2) | (3) | (5) | (25) | (37) | |
| | (2) | (3) | (4) | (24) | (35) | |

| Name | DOB | Patient Address | Chief Complaint | Disposition | Incident Address | Unit | Options |
|---|---|---|---|---|---|---|---|
| | | | Nausea/Vomiting (Unknown Etiology) | Treated Transported by EMS UNIVERSITY HOSP UCSD MED CENTE - 50 | | E1/ | |

| | | | | | | Welcome Ame! [Log Out] | |
|---|---|---|---|---|---|---|---|
| Dashboard | 🚒 / | FS | 91137 | 08/19/2012 12:45 | | Psych / Suicide Attempt (L1) | Level 1 Medical - SHARP MEMORIAL HOSPITAL - 40 | M11, E23, M66 |
| CAD | 🚒 | FS | 91136 | 08/19/2012 12:42 | | Electrical Short | Level 2 Fire | z2511 |
| Patient Search | 🚒 | FS | 91135 | 08/19/2012 12:41 | | Unc/Fainting (Non Trauma) (L1) | Level 1 Medical - SHARP MEMORIAL HOSPITAL - 40 | E28, M37 |
| Managed | | | | | | | | |
| Algorithms | | FS | 91134 | 08/19/2012 12:37 | 06th Ave & Grape St | Unknown Problem (Man Down) (L1) | Level 1 Medical - MERCY HOSPITAL - 50 | M12, E3 |
| Action Items | 🚒 | FS | 91132 | 08/19/2012 12:27 | | Sick Person (Specific Dx) (L4) | Level 4 Medical - SCRIPPS MEMORIAL - 30 | E42, MR40, BLS21, E42, MR33 |
| My Profile | | | | | | | | |
| Admin | 🚒 | FS | 91133 | 08/19/2012 12:27 | | Falls / Back Inj (Trauma) (L1) | Level 1 Medical | T10, M229 |
| Change Password | 🚒 | FS | 91130 | 08/19/2012 12:14 | | Diabetic Problems (L1) | Level 1 Medical - UNIVERSITY HOSP UCSD MED CENTE - 50 | E4, M37, M60 |
| | 🚒 / | FS | 91129 | 08/19/2012 12:13 | | Headache (L1) | Level 1 Medical - PARADISE VALLEY HOSPITAL - 50 | E7, M32 |
| | 🚒 / | FS | 91127 | 08/19/2012 12:10 | 0 1-8 Wb | Traffic Accident (L1) | Level 1 Medical - SHARP MEMORIAL HOSPITAL - 40 | MR39, E15 |
| | 🚒 | FS | 91125 | 08/19/2012 12:01 | Sea World Dr | Heart Problems (L1) | Level 1 Medical - SCRIPPS MEMORIAL HOSPITAL - 20 | E20, M35 |
| | 🚒 | FS | 91122 | 08/19/2012 11:58 | | Chest Pain (L1) | Level 1 Medical - ALVARADO HOSPITAL - 30 | E10, M1 |
| | 🚒 | FS | 91124 | 08/19/2012 11:57 | | Falls / Back Inj (Trauma) (L1) | Level 1 Medical - SCRIPPS MEMORIAL - 40 | E90, MR9 LG |
| | 🚒 / | FS | 91117 | 08/19/2012 11:42 | | Sick Person (Specific Dx) (L3) | Level 3 Medical - UNIVERSITY HOSP UCSD MED CENTE - 50 | E17, M31 |
| | 🚒 / | FS | 91110 | 08/19/2012 11:20 | | Sick Person (Specific Dx) (L3) | Level 3 Medical - MERCY HOSPITAL - 50 | E22, M20 |

FIG. 9

| | | | | | | | |
|---|---|---|---|---|---|---|---|
| Dashboard | | FS | 91137 | 08/19/2012 12:45 | | Psych / Suicide Attempt (L1) | Level 1 Medical - SHARP MEMORIAL HOSPITAL - 40 | M11, E23, M66 |
| CAD | | FS | 91136 | 08/19/2012 12:42 | | Electrical Short | Level 2 Fire | z2511 |
| Patient Search | | FS | 91135 | 08/19/2012 12:41 | | Unc/Fainting (Non Trauma) (L1) | Level 1 Medical - SHARP MEMORIAL HOSPITAL - 40 | E28, M37 |
| Managed Algorithms | | FS | 91134 | 08/19/2012 12:37 | 06th Ave & Grape St | Unknown Problem (Man Down) (L1) | Level 1 Medical - MERCY HOSPITAL - 50 | M12, E3 |
| Action Items | | FS | 91132 | 08/19/2012 12:27 | | Sick Person (Specific Dx) (L4) | Level 4 Medical - SCRIPPS MEMORIAL - 30 | E42, MR40, BLS21, E42, MR33 |
| My Profile | | FS | 91133 | 08/19/2012 12:27 | | Falls / Back Inj (Trauma) (L1) | Level 1 Medical | T10, M229 |
| Admin | | FS | 91130 | 08/19/2012 12:14 | | Diabetic Problems (L1) | Level 1 Medical - UNIVERSITY HOSP UCSD MED CENTE - 50 | E4, M37, M60 |
| Change Password | | FS | 91129 | 08/19/2012 12:13 | | Headache (L1) | Level 1 Medical - PARADISE VALLEY HOSPITAL - 50 | E7, M32 |
| | | FS | 91127 | 08/19/2012 12:10 | 0 1-8 Wb | Traffic Accident (L1) | Level 1 Medical - SHARP MEMORIAL HOSPITAL - 40 | MR39, E15 |
| | | FS | 91125 | 08/19/2012 12:01 | Sea World Dr | Heart Problems (L1) | Level 1 Medical - SCRIPPS MEMORIAL HOSPITAL - 20 | E20, M35 |
| | | FS | 91122 | 08/19/2012 11:58 | | Chest Pain (L1) | Level 1 Medical - ALVARADO HOSPITAL - 30 | E10, M1 |
| | | FS | 91124 | 08/19/2012 11:57 | | Falls / Back Inj (Trauma) (L1) | Level 1 Medical - SCRIPPS MEMORIAL - 40 | E90, MR9 LG |
| | | FS | 91117 | 08/19/2012 11:42 | | Sick Person (Specific Dx) (L3) | Level 3 Medical - UNIVERSITY HOSP UCSD MED CENTE - 50 | E17, M31 |
| | | FS | 91110 | 08/19/2012 11:20 | | Sick Person (Specific Dx) (L3) | Level 3 Medical - MERCY HOSPITAL - 50 | E22, M20 |

Behavioral/Psych

| Patient Name | # Of Incidents ⇩ | # Of Related Incidents | Is Homeless? | SDPD At Scene Count | PERT At Scene Count |
|---|---|---|---|---|---|
| | 152 | 114 | N | 31 | 0 |
| | 101 | 18 | Y | 34 | 0 |
| | 63 | 3 | Y | 10 | 0 |
| | 58 | 31 | Y | 4 | 1 |
| | 48 | 2 | Y | 5 | 0 |
| | 47 | 3 | Y | 10 | 1 |
| | 46 | 1 | N | 0 | 0 |
| | 42 | 10 | N | 7 | 0 |

*FIG. 10*

In-Home Difficulties

| Address | Common Patient Name | Common DOB | Related Events ⇨ | CAD Events | ePCR Events | Mobility/Fall Involved | Total Transports |
|---|---|---|---|---|---|---|---|
| Dr SAN DIEGO, CA | | | 24 | 38 | 24 | 6 | 7 |
| Dr SAN DIEGO, CA | | | 16 | 18 | 15 | 18 | 0 |
| SAN DIEGO, CA | | | 14 | 17 | 5 | 18 | 0 |

FIG. 12

| Unit Type | Count | Time Spent (Hours) | | Estimated Cost |
|---|---|---|---|---|
| | | Total | Average | |
| AMBULANCE | 70 | 58:25 | 00:50 | $ 102,871.75 |
| ENGINE | 57 | 15:15 | 00:16 | $ 4,925.75 |
| TRUCK | 4 | 00:52 | 00:13 | $ 294.67 |
| Totals | 131 | 75:32 | 00:34 | $ 108,092.17 |

Algorithm Detail

INFOTECH SYSTEMS MANAGEMENT — *AGENCY PORTAL*

Welcome Anne! [ Log Out ]

- Dashboard
- CAD
- Patient Search
  - Managed
- Algorithms
- Action Items
- My Profile
- Admin

Serial Inebriate

| Patient Name | # Of Incidents ⇩ | # Of Related Incidents | # Of Related Incidents (Last 30 Days) | Is Homeless? | SDPD At Scene Count | PERT At Scene Count |
|---|---|---|---|---|---|---|
| | 63 | 45 | 1 | Y | 10 | 0 |
| | 47 | 26 | 0 | Y | 10 | 1 |
| | 33 | 11 | 0 | Y | 9 | 0 |
| | 31 | 17 | 0 | Y | 7 | 0 |
| | 31 | 17 | 2 | Y | 7 | 0 |
| | 29 | 20 | 0 | N | 12 | 0 |
| | 26 | 13 | 0 | Y | 2 | 1 |
| | 26 | 14 | 0 | Y | 10 | 0 |
| | 26 | 15 | 0 | Y | 6 | 0 |
| | 26 | 20 | 4 | Y | 8 | 0 |
| | 25 | 21 | 1 | Y | 7 | 1 |
| | 25 | 14 | 0 | Y | 6 | 0 |
| | 24 | 16 | 0 | Y | 11 | 0 |
| | 21 | 17 | 0 | Y | 5 | 0 |
| | 21 | 17 | 0 | Y | 10 | 1 |
| | 19 | 15 | 0 | N | 8 | 3 |
| | 18 | 11 | 3 | N | 3 | 1 |
| | 18 | 8 | 0 | N | 3 | 8 |
| | 18 | 9 | 1 | Y | 6 | 0 |
| | 17 | 13 | 8 | Y | 4 | 8 |
| | 17 | 16 | 0 | Y | 10 | 0 |
| | 17 | 7 | 0 | N | 6 | 0 |
| | 15 | 7 | 1 | Y | 3 | 1 |
| | 14 | 7 | | | 4 | |

Top Chief Complaints
Other ( 18 )
Respiratory Distress ( 14 )
ETOH Abuse ( 3 )
Other Illness/Injury ( 3 )
Weakness ( 3 )

Top Hospital Destinations
UNIVERSITY HOSP UCSD MED CENTE ( 33 )
MERCY HOSPITAL ( 11 )
PARADISE VALLEY HOSPITAL ( 1 )

Top Calling Locations
XXXX C St SAN DIEGO, CA 92101 ( 23 )
XXXX PARK Bl SAN DIEGO, CA 92101 ( 3 )
Park Bl Broadway San Diego, CA 92101 ( 3 )
XXXX BROADWAY SAN DIEGO, CA 92101 ( 2 )
XXX Park Bl San Diego, CA 92101 ( 2 )

Total 9-1-1 Encounters: 48
Total Ambulance Mileage: 171

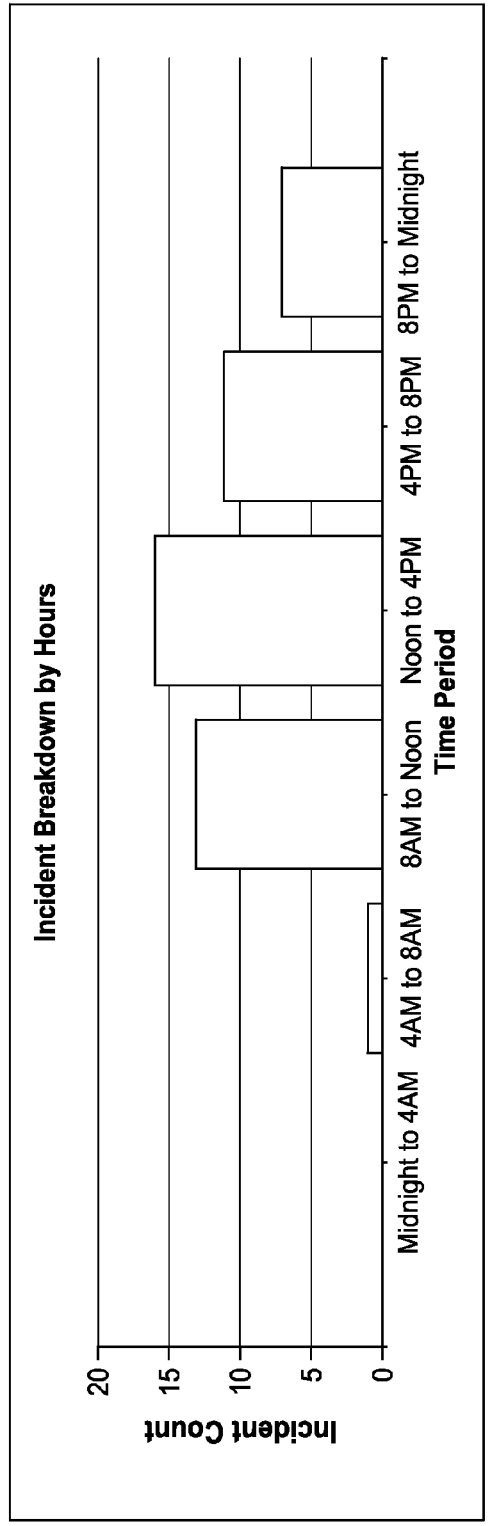

FIG. 15

EMERGENCY INCIDENT CATEGORIZATION AND ALERTING

CROSS-REFERENCE TO RELATED APPLICATIONS

This application claims priority to U.S. Provisional Application No. 61/883,390, filed Sep. 27, 2013, which is incorporated by reference in its entirety. Any and all priority claims identified in the Application Data Sheet, or any correction thereto, are hereby incorporated by reference under 37 C.F.R. §1.57.

BACKGROUND

1. Field

The technical field relates generally to care giver services and methods and devices for efficiently and quickly allocating care giver services.

2. Description of the Related Art

Emergency first responders are usually tasked with responding to whatever emergency or threat presents itself, without the benefit of time to determine the gravity of the situation or the most efficient course of action. For example, a 9-1-1 call requesting paramedics will usually be answered repeatedly with 9-1-1 paramedics, even if the caller is a repeat caller whose needs are more appropriately met by psychiatric help or non-emergency primary medical care. In either case, important public funds and resources are wasted, all while the individual receives care that is inferior to his or her actual needs.

SUMMARY

One embodiment includes a method for emergency service contact alerting, the method comprising receiving an electronic report input associated with an incident or individual, categorizing the electronic report input with a matching engine and a database based on a person identifier, the matching engine configured to assign one or more categorization attributes corresponding to frequency or priority of the incident or individual, and generating an alert provision instruction to one or more specialized caregiver devices based on the one or more categorization attributes.

Another embodiment includes an emergency service device comprising a receiver configured to receive an electronic report input associated with an incident or individual, an incident processor configured to match a person identifier from the electronic report input with person-centric data from a database, wherein the matching comprises assigning one or more categorization attributes corresponding to frequency or priority of the incident or individual, and an alert transmitter configured to generate an alert for transmission to one or more specialized caregiver devices based on the matched individual.

BRIEF DESCRIPTION OF THE DRAWINGS

These or other aspects will become apparent and more readily appreciated from the following drawings, which taken in conjunction with the Detailed Description section and other sections of the present application, serve to explain the principles of the present disclosure.

FIG. 2 is a screenshot illustrating various identifiers that can be used to match multiple incidents to particular individuals according to at least one embodiment.

FIG. 4 is a screenshot of a dashboard with ranked users according to at least one embodiment.

FIG. 6 is a screenshot illustrating a configuration interface for incident processing.

FIG. 8 is a screenshot illustrating a real-time Computer-Aided Dispatch system according to at least one embodiment.

FIG. 9 is a screenshot of a 9-1-1 live feed according to at least one embodiment.

FIG. 10 is a screenshot of a category of individuals and data for each according to at least one embodiment.

FIG. 12 is a screenshot of in home difficulties according to at least one embodiment.

FIG. 13 is a screenshot of a real-time cost assessment according to at least one embodiment.

FIG. 14 is a screenshot of serial inebriated identification according to at least one embodiment.

FIG. 15 is a screenshot of trend tracking according to at least one embodiment.

Figure 1:
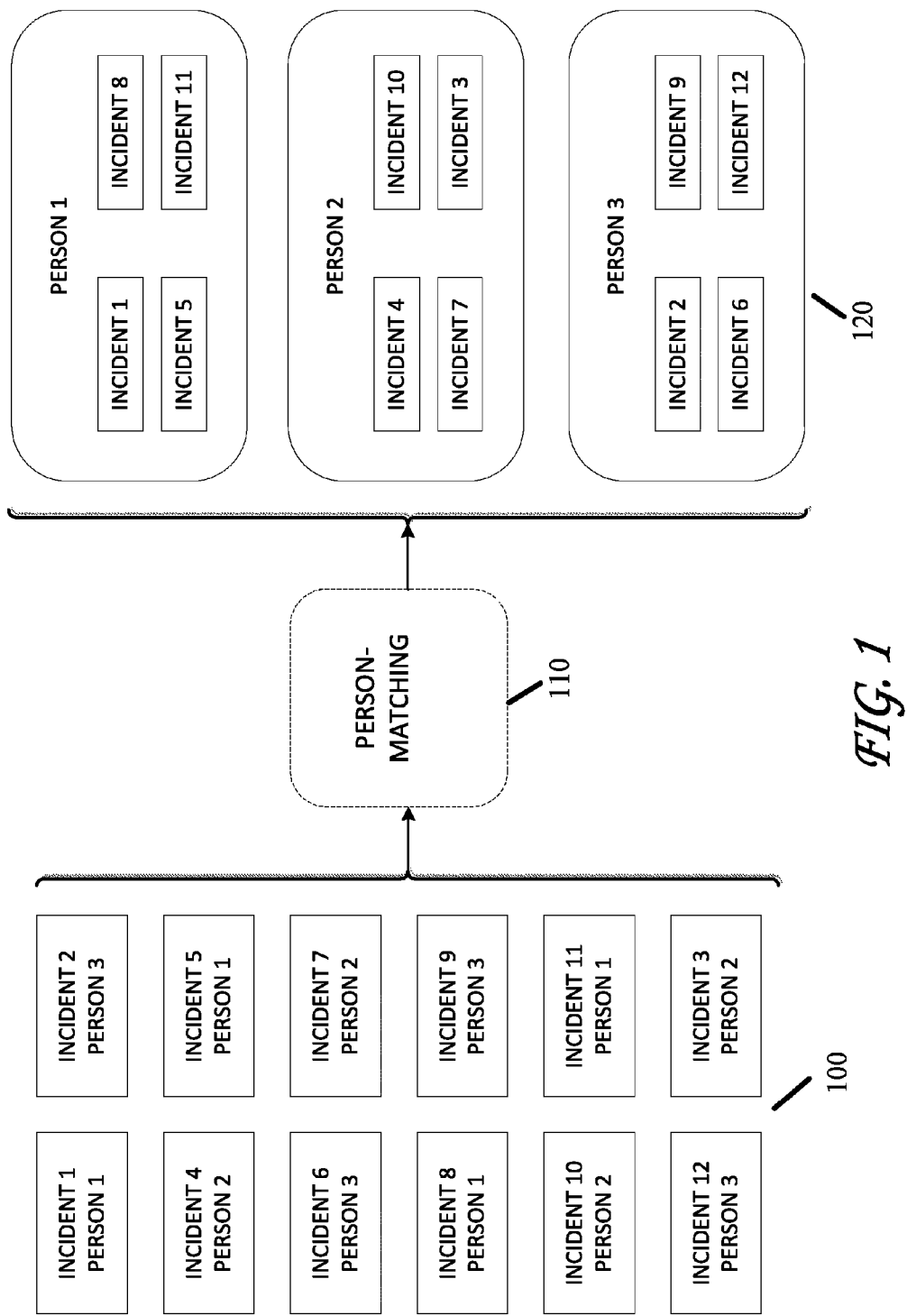
FIG. 1 shows a functional block diagram of a system for grouping applying an algorithm to unassociated incidences involving different individuals in order to associate multiple incidences with particular individuals according to at least one embodiment.

The various features illustrated in the drawings may not be drawn to scale. Accordingly, the dimensions of the various features may be arbitrarily expanded or reduced for clarity. In addition, some of the drawings may not depict all of the components of a given system, method, or device. Finally, like reference numerals may be used to denote like features throughout the specification and figures.

Various implementations of systems, methods and devices within the scope of the appended claims each have several aspects, no single one of which is solely responsible for the desirable attributes described herein. Without limiting the scope of the appended claims, some prominent features are described herein.

DETAILED DESCRIPTION

As the public's safety net, emergency response agencies are subject to unique constraints and professional standards of care that result in documentation and operational methods that are very different from other traditional care providers. Response agencies document their activity in an incident-centric manner, fulfilling their primary role to provide, document, assess and improve upon time-dependent life-saving interventions during an isolated incident. As a result of this incident-centric response, documentation, and access to information, emergency responders are usually tasked with providing care in a variety of emergencies with unknown circumstances, and without the benefit of time or situational context to determine the most appropriate or efficient course of action. For example, a 9-1-1 call requesting paramedics is usually answered consistently with 9-1-1 paramedics, even if the caller is a repetitive caller who is not experiencing an emergency, or whose needs are more appropriately met by psychiatric help or non-emergency care. Often, the responding paramedics do not know they are responding to a repetitive caller, because the nature of incident-centric response in a dynamic 9-1-1 setting has deployed a different paramedic each time. Each paramedic provides a new assessment and treats the patient without knowledge of prior care from peers. As a result, important safety-net resources are wasted, all while the individual receives care that is unsuited to his or her actual needs. Some embodiments of the present disclosure are directed toward a system for identifying individuals who have unique needs, to provide patient-centric care, despite an incident-centric response. Such individuals may include those needing psychiatric help, those who are homeless, and those who suffer from chronic social or medical vulnerabilities. In some cases, a real medical emergency may be the cause of an emergency response; however, knowing that the individual in need suffers from a particular chronic condition will aid the paramedics or other medical personnel in delivering the best care possible using the least amount of valuable public time and money.

The disclosure herein includes features for overseeing and/or surveillance for the purpose of identifying and providing services to vulnerable individuals, or for forming strategic initiatives for community issues. One non-limiting advantage of the disclosed features takes the former arduous work of medical chart review to extract knowledge in near real-time, and provides information in an actionable time frame. Another non-limiting advantage of the disclosed features is reducing or eliminating the months of lag time typically needed to pinpoint community issues after the fact, and gives a response agency systemic situational awareness about what is going on in their city at any time. Based on contacts with emergency services as recorded in incident records, patient care records, medical records, or other reports, individuals can be identified, monitored, and categorized. Such identification, monitoring, and categorization can then be used to alert the appropriate services to provide a meaningful response to a current or subsequent encounter with the individual.

The disclosure herein includes features for prioritizing patients. Prioritization may be based on the information generated by the described systems and methods such as the categorization of an individual, the categorization of a location, or a combination thereof. For example, a given category may be associated with a priority level such that incidents, locations, or patient within the category are given priority. The priority may be given in terms of alerting, dispatching a response, display on a status dashboard, or a combination thereof. In some embodiments, the user interface may include a map displaying patient locations, their priority levels, their activities, interventions taken or requested, or other information relevant to the patients located on the map.

The disclosure herein also includes features for mapping of patient locations. When prioritizing patients, the system may determine which patient is more vulnerable or in more acute conditions that increases the likelihood of requiring more attention or response, as compared to other patients in the system. The system may update patient priorities as it receives more data (e.g., incident reports, dispatch reports, medical records). The system may be integrated with case management and reporting features described herein, which may further be integrated with existing task management or calendar technologies.

FIG. 1 illustrates a method or a system, according to some embodiments of the present disclosure, of correlating various incidences with particular individuals. Often there are a group of seemingly unrelated incidences 100. The incidences 100 involve any number of individuals some of whom may have been involved in multiple incidences. Nevertheless, the record of each instance may not be correlated with any other incidence even if the same or related individuals were involved. Thus, in some embodiments, an algorithm, such a person-matching algorithm 110 is applied to the incidences 110 to correlate the incidences 100. The result, in some embodiments, is a correlation 120 between different individuals and the various incidences involving each individual.

An incident may be documented in a variety of formats. As information systems and network connectivity become increasingly available, digital records provide an attractive method for collecting, sharing, and storing data. One way to document an incident is via an electronic care report. A care report may include a checklist or notes from a service provider such as a firefighter, a peace officer, a paramedic, or a health care professional involved with the incident. The care report may be entered using a communication device such as a laptop computer, smartphone, tablet computer, desktop computer, set-top-box, or other similar devices. The communication device may be configured to prompt the service provider for the information to be included in the care report. In some implementations, the report may include a physical written report. In such implementations, the system may receive the paper document, obtain an image of the document, and generate a digital record based on the scanned information. Examples of the information included in a care record will be discussed in further detail below such as in reference to FIG. 2.

As an illustration, FIG. 1 shows that a person referred to as "PERSON 1" is associated with INCIDENCES 1, 5, 8, and 11; however, prior to a matching algorithm being applied to the incidences 100, there may have been no reason to associate the various incidences with PERSON 1. Similar, FIG. 1 demonstrates that PERSON 2 is associated with INCIDENCES 4, 7, 10, and 3. And PERSON 3 is associated with INCIDENCES 2, 6, 9, and 12. With these various correlations in hand, a medical professional may be able to draw conclusions, general or specific, about any particular individual. For example, if INCIDENCES 1, 5, 8, and 11 are all or mostly all heart related, a medical professional may be able to determine that PERSON 1 has a poorly managed heart condition. This information may be used to recommend to PERSON 1 that he or she consult or increase visits to a heart specialist. And, in some cases, if PERSON 1 is involved in another medical emergency, this information may be used deliver targeted health care to PERSON 1 rather than spending needless resources to determine the nature of the emergency as if this were the first time PERSON 1 were needing medical attention.

FIG. 1 has been illustrated to show a correlation or connection between various incidences 100 based on the individuals involved in each incidence. Person-matching algorithm 110 may be based on any number of personal identifiers, which can include but are not limited to, those shown in FIG. 2.

FIG. 2 illustrates a screenshot of a program configured to access a database containing information, such as incidences 100, and perform an algorithm, such as person-matching algorithm 110, to produce data files containing correlations of incidences 120 based on, for example, the identities of the individuals involved in any given incidence.

As shown in FIG. 2, various personal identifiers may be used to correlate various incidences. Such identifiers may include, but are not limited to, social security number, parts of a social security number, date of birth, first name, last name, alias names, gender or sex, parts of a name, address, street names, physical characteristics, the sound of a name, a social or medical vulnerability, or behavioral patterns. Moreover, in some embodiments, additional identifiers and/or combinations of the above identifiers could be used as the basis to identify related incidents.

According to some embodiments, the attempt to match multiple incidents associated with the same person begins at the first criterion level, moving down to the next level if the previous does not result in a match. With each step down, the accuracy of the match decreases, beginning with the most stringent matching requirements (based on accepted identifiers) and ending with matches based on combinations of identifiers, social or medical history, and behavior during the 9-1-1 call. The user may select the level at which they classify the match as being "high level" or "low level," for alerting purposes (as discussed later, a person may choose to withhold alerts for low-level matches).

Figure 3:
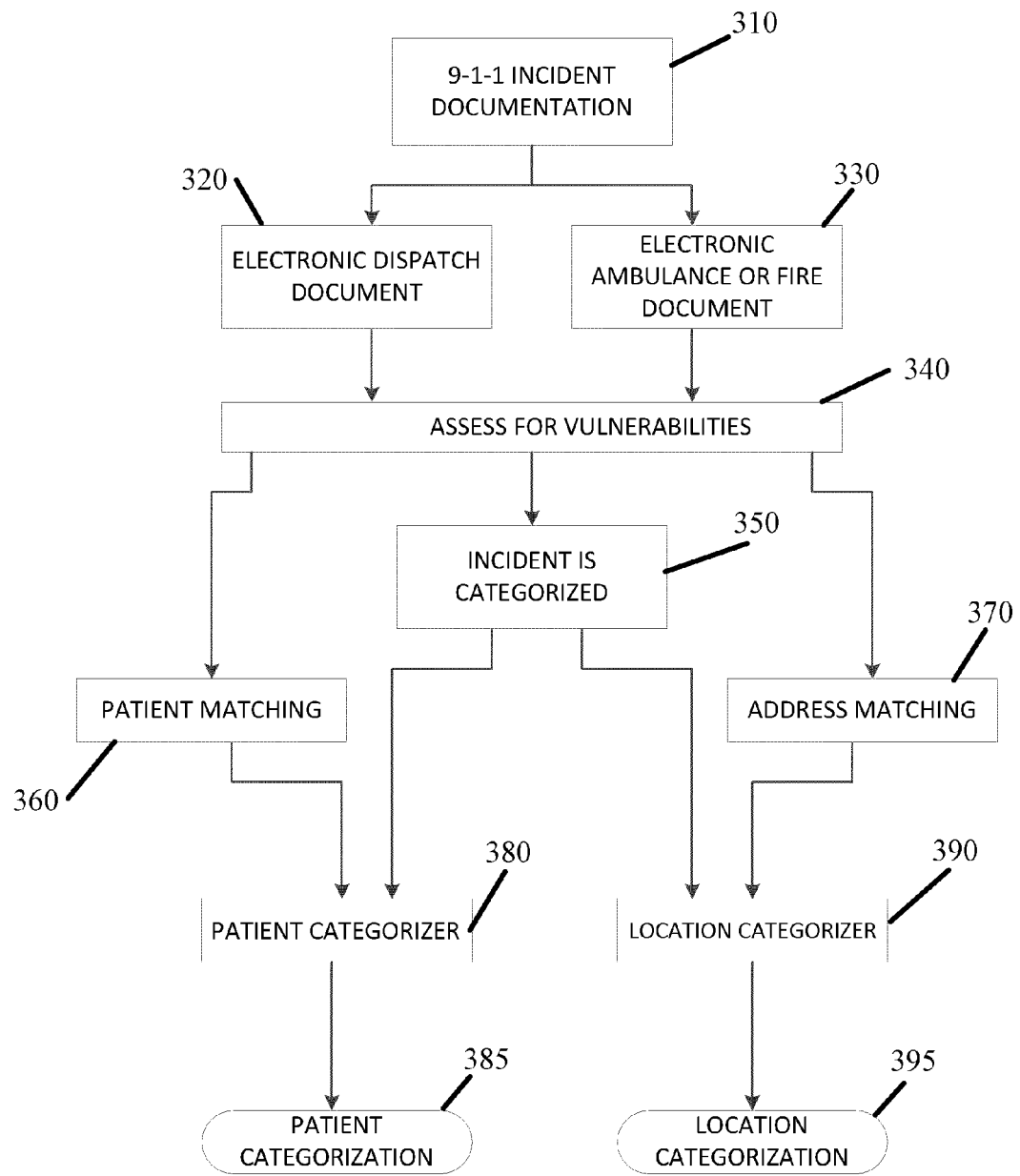
FIG. 3 illustrates a process flow diagram for a method of categorizing incidents incorporating innovative aspects of the present disclosure.

FIG. 3 illustrates a process flow diagram for a method of categorizing incidents incorporating innovative aspects of the present disclosure. In some embodiments, a process begins with receipt of a report for an initial event or emergency event, such a 9-1-1 call at block 310. The report is then provided to various emergency responders at blocks 320 and 330. Specifically, at block 320, dispatch information is generated from the report. The dispatch information may be included in a dispatch document. The dispatch document is generally accessed and used by a dispatcher. At block 330, first responder information is provided based on the report. The first responder information may be included in an ambulance or fire document. The ambulance or fire document may be generally accessed and used by the first responders, which may be paramedics, firefighters, etc. Each report is tailored to the response type provided. However, as the initial incident typically is received at a call center, the appropriate response(s) may be unknown at first. Similarly, information important for dispatchers may differ from the information needed by a first responder. Furthermore, case management and reporting features described herein may be integrated with existing task management technologies and calendar functions.

One or both of the dispatch information and the first responder information are provided to block 340 for vulnerability assessment. The vulnerability assessment identifies vulnerabilities or populations of interest. Examples of vulnerabilities include homelessness, chronic respiratory disease, drug dependency, psychiatric conditions and fall-risks. Examples of populations of interest include pediatrics, geriatrics, veterans and insurance-based populations. The identification may be based on a comparison of dispatch information and the first responder information, or independently on either dispatch or first responder information. In some implementations, the assessment may be based on several incident documents. In such an implementation, multiple reports may be obtained for processing and analysis. In some implementations, the assessment may utilize a database of previously identified vulnerabilities and/or populations of interest. For example, a location may be notoriously dangerous, generating many previous incident reports. As such, a database may include a vulnerability record identifying the location as one of vulnerability. When a new incident is received for the location, the incident or patient may be properly associated with the vulnerability.

In some embodiments, there are at least three components that can be algorithmically categorized: (1) Incident Categorization at block 350, (2) Patient Categorizing at block 360, and (3) Address Categorization at block 370.

At block 350, an incident is categorized if at block 340, the presence of a vulnerability is identified. In such instances, the current 9-1-1 incident will be categorized with that vulnerability, regardless of whether the patient's identity is known. Such categorization may be valuable in generating an effective response. For example, the category of the incident can be used: (a) to decide whether an alert should be sent (for example: if a case manager only wants to be notified if the patient is intoxicated, rather than receive an alert each time he calls 9-1-1); (b) to determine the strain that a specific social vulnerability has on the 9-1-1 system (for example: non-medical falls or alcohol related incidents); (c) to assist with patient matching in the absence of suitable patient identifiers (in some cases, the match is based on limited identifiers in combination with behavioral or medical indicators); and/or (d) to contribute to the categorization of an individual, residence, or facility. In some embodiments, similar or additional options will be available. Examples of categories which may be used to categorize an incident include alcohol, congestive heart failure, psychiatric, homeless, diabetic and stroke-based incidents.

At block 360, patient matching is performed. Patient matching attempts to identify one or more persons who may have previously been involved in an incident. The patient matching may be based on name, social security number, driver's license number, physical characteristics (e.g., height, weight, hair color, tattoos or other permanent bodily features, and the like), location, phone number, etc. The patient matching may obtain the characteristics for the current incident from the dispatch or first responder reports and search a database of prior incidents. Such search may be based on, among others, alias names and street names. In some implementations, one patient may be found. In some implementations, there may be several possible matches. In one example implementation, the set of matches may be provided along with a match score indicating how well a particular member of the set matches the current incident information. Sometimes first-responder records for the same person are grossly different (as some people have identity disorders or are deliberately giving untrue information); the matching process is able to adapt for future incidents once the identities are manually merged through the user interface, for example.

At block 380, the identified patient(s) may be categorized to: (a) determine the presence of a vulnerability in the individual (for example: drug dependence, behavioral/psychiatric, homeless, fall-risk); and/or (b) identify populations of interest (for example: chronic pediatric patient, veteran, etc.). Most patient categorization is dependent upon incident category and can be based on a threshold of categorization counts before the individual obtains a label. The result of patient identification of block 380 is one or more patient categorizations 385. The patient categorization information may be associated with the incident documentation to facilitate the emergency response. In some implementations, the categorization may be stored remotely or locally for future use in categorizing and identifying information for future incidents.

At block 370, address matching may be performed. The address matching attempts to identify an address for the incident based on the received incident information. The matching may use a database of previous locations. In some implementations, the address matching may consult a geocoding service accessible via a network such as Google® Maps. In some implementations, one address may be found. In some implementations, there may be several possible matches, such as a range of street numbers or a list of streets in the vicinity. In this case, the set of hits may be provided along with a match score indicating how well a particular member of the set matches the current incident information.

At block 390, an address is categorized based on the incident categorization and/or the address match identified at block 370. The categorization may: (a) identify private residences with potential risks (fall-risk address, elderly issues in the home); (b) identify facilities that are high utilizers of emergency services (nursing homes with improper use of 9-1-1); and/or (c) assist in understanding the total impact of an individual's 9-1-1 usage in the absence of non-medical 9-1-1 responses (for example: not all 9-1-1 calls will generate a report with patient identifiers. This usage of an address can be linked to the person who has generated a previous or latter medical report to understand total 9-1-1 use). The result of location categorization at block 390 is one or more location categorizations 395. In some embodiments, address categorization 395 is dependent upon incident categorization 350.

FIG. 4 illustrates a screenshot of a dashboard with ranked users according to at least one embodiment. A dashboard is shown which ranks various users. The members of different groups, e.g., homeless individuals or psychiatric users, and the frequency of their emergency incidences are displayed. The information presented may be obtained from a database which stores the information generated via the process shown in FIG. 3. Additionally, the records and frequency data may be grouped or filtered according to various time intervals of interest, such as last week, last 2 weeks, last month, last 6 months, last year, etc. Other time intervals may also be used depending on the data of interest. The data shown in FIG. 4 may also be sorted by one or more determined vulnerability as discussed in reference to FIG. 3. (Other embodiments could rank based on minutes spent, rather than count of 9-1-1 calls). How the users are ranked may reflect the relative prioritization for a given user.

Figure 5:
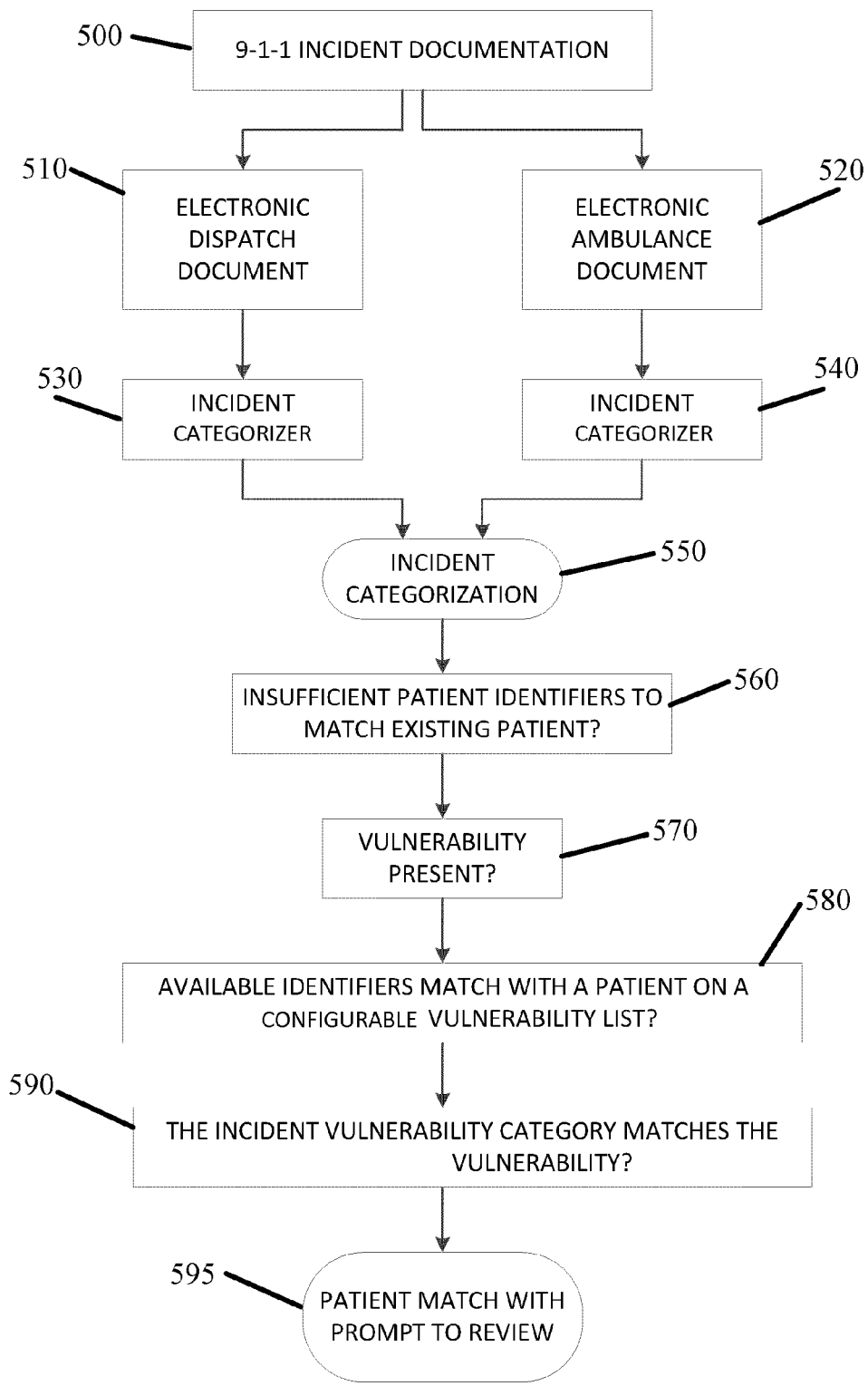
FIG. 5 illustrates a process flow diagram of a method for processing incident information including innovative features of the present disclosure.

FIG. 5 illustrates a process flow diagram of a method for processing incident information including innovative features of the present disclosure. In the absence of sufficient identifiers included in the incident document, an identity match can occur if there are partial identifiers and common behavioral or medical tendencies. For example, first responders who are responding to an incident based on 9-1-1 incident documentation generated at block 500 frequently are associated with an intoxicated patient who is unconscious and/or unable to provide information about them. At blocks 530 and 540, the incident is categorized based on the dispatch document and first responder document (respectively), such as is described in reference to FIG. 3. An incident categorization is generated at block 550 based on the information received from the respective incident categorizations of blocks 530 and 540. At block 560, a determination is made as to whether sufficient information to identify a patient has been received. If the patient has been identified, the process ends. If the patient has not been identified, ending the process would mean that no information about the incident is provided. However, as one non-limiting advantage of the features describe, further processing based on vulnerability may be used to identify unidentifiable patients.

At block 570, one or more vulnerability can be determined based on the received incident information. One or more vulnerabilities are determined for the incident by comparing information for the incident to a list of known vulnerabilities. The known vulnerabilities and matching criteria may be stored in a database. Examples vulnerabilities include drug dependence, behavioral/psychiatric, homeless, and fall-risk. If no vulnerability is identified, the process may end. In such instances, the amount of information needed to make an assessment for the incident is insufficient. However, if at least one vulnerability is identified for the incident, the process continues to block 580.

According to the example process shown in FIG. 5, at block 580, a determination is made as to whether the available identifiers included in the incident information matches with a patient previously associated with at least one vulnerability. If so, at block 590 a determination is made as to whether the incident vulnerability matches with one of the patients identified at block 580. If so, a match may have been identified. Accordingly, at block 595, because this is likely to be considered a low-level match, the system flags the identification for review, with the option to link and/or unlink the incident and patient. FIG. 6 is a screenshot illustrating these options and capabilities.

Figure 7A:
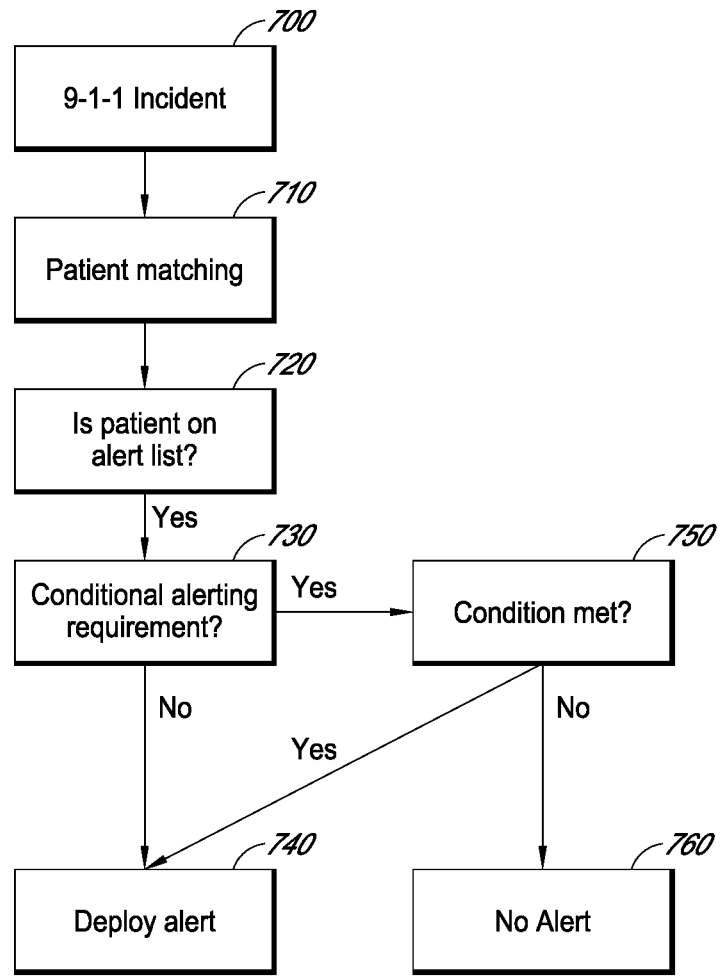
FIG. 7A is a process flow diagram of method of conditional alerting according to at least one embodiment.

FIG. 7A is a process flow diagram of a method of conditional alerting. Alerts may be used in an EMS system to notify case managers or first responders when particular patients call 9-1-1. Conditional alerts are a modification of these alerts, which are associated with criteria or behavior indicating whether or not an alert should be sent. Conditions may be applied to comply with the Health Insurance Portability and Accountability Act (HIPAA) regulations by eliminating unnecessary and/or potentially illegal disclosure of a patient's information. For example, alerts to an alcohol treatment program may need to be restricted to alcohol-related 9-1-1 incidents, while alerts related to general medical calls should be withheld. In some cases, certain doctors may only want alerts for particular medical conditions. Conditional alerts can be dependent upon patient matching, as well as incident categorization provided by vulnerability-specific methods described herein. Conditional alerting can provide one non-limiting advantage of reducing the resources used in providing emergency services. For example, suppressing redundant alerts or alerts which may have been delivered via another communication channel can reduce the amount of alerting traffic. This also allows the emergency service devices receiving the alerts spend resources efficiently to handle alerts which may be actionable rather than informational or "noise." This may be particularly important for emergency service devices which are field operated devices (e.g., deployed in ambulance or as a handheld device carried by an EMT). Such field operated devices may be subject to power, space, processing, memory and bandwidth limits.

According to some embodiments, a 9-1-1 incident 700 triggers a patient matching at block 710. The patient matching may be similar to the patient matching describe in FIG. 3 or 5. As an initial alert check, at block 720 a determination is made as to whether a patient is on an alert list. If the determination is negative, no alert is sent for the incident. However, if the determination at block 720 is affirmative, a determination as to whether there is a conditional alerting requirement(s) is performed at block 730. If the answer to that question is "no," an alert may be generated and transmitted at block 740. Returning to determination block 730, if additional alerting requirements are identified for the patient, at block 750 a determination is made as to whether the additional conditions are met. If the determination at block 750 is affirmative, an alert may be generated and transmitted at block 740. If the determination at block 750 is negative, the process terminates at block 760 without generating or transmitting an alert.

For example, the system implementing the process of FIG. 7A may receive a 9-1-1 call corresponding to the 9-1-1 incident 700 illustrated in FIG. 7A. At block 710 the system may determine, based on the phone number and the location and time of the call, that the call is coming from a frequent 9-1-1 caller who often gets drunk at a certain location at a certain time and dials 9-1-1 often. In some implementations, location may not provide the desired level of reliability for matching, categorizing, and alerting. In such implementations, the matching at block 710 may include mining the medical report or incident report (if available) to see if there is an indication of the caller being intoxicated. Such indication may be based on vital sign entries included in the report, mental assessment information included in the report, or other information collected for the caller. The system may further determine, as illustrated in block 720 that this patient is on, among others, an alert list for an alcohol treatment program. This determination may be made based on a stored list of individuals who are included in the program. The matching at block 710 provides the identification information needed to perform the determination at block 720. It will be appreciated that a name or social security number may not be needed to match an individual. Patterns of behavior, conditions, locations, and the like as recorded in the received report(s) may be used to generate a high-probability identification for an individual. This allows the system to operate securely and accurately using reports which may be redacted or otherwise protected under privacy or other statutory or contractual provisions. At block 730, the system determines that this alcohol treatment program alert is a conditional alerting, and at block 750 the system further determines that the condition is met since the caller is calling from his oft-visited bar at near midnight. The system then would deploy alert as illustrated in block 740 since the condition for the alert is met in this example.

In another example, the system may determine based on the phone number and associated medical reports in the system to see if there is an indication of whether the caller being intoxicated. The medical reports may include records regarding a variety of vital signs such as mental assessment.

Figure 7B:
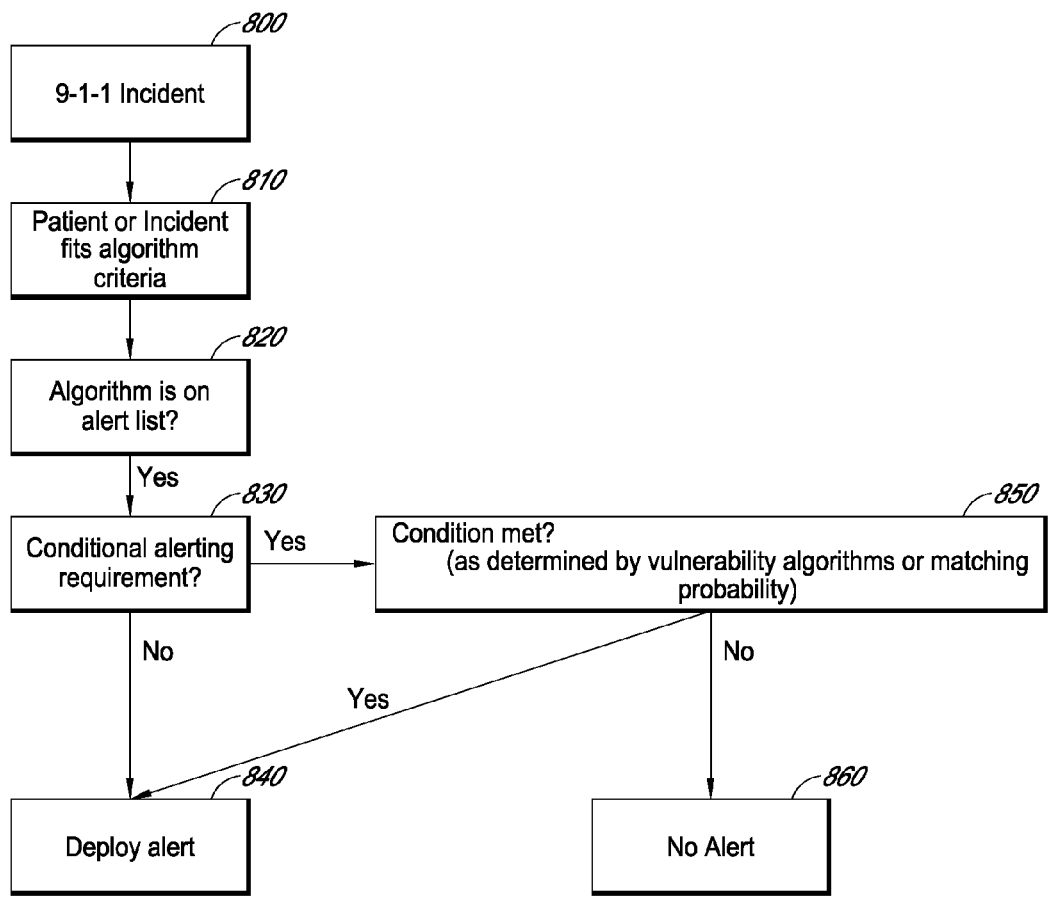
FIG. 7B is a process flow diagram of a method of group alerting.
Figure 11:
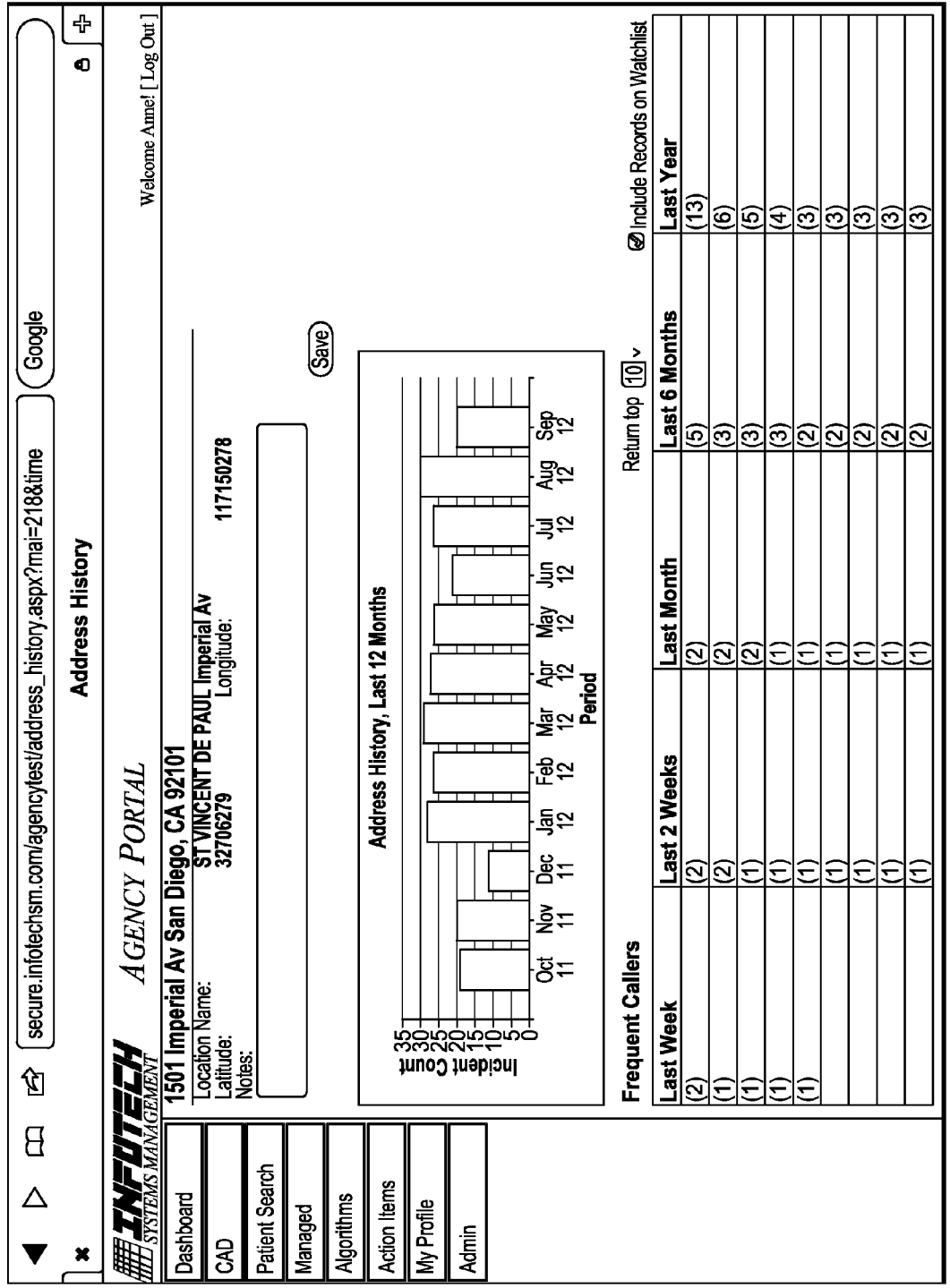
FIG. 11 is a screenshot of a hot-spot location zoom in according to at least one embodiment.
Figure 16:
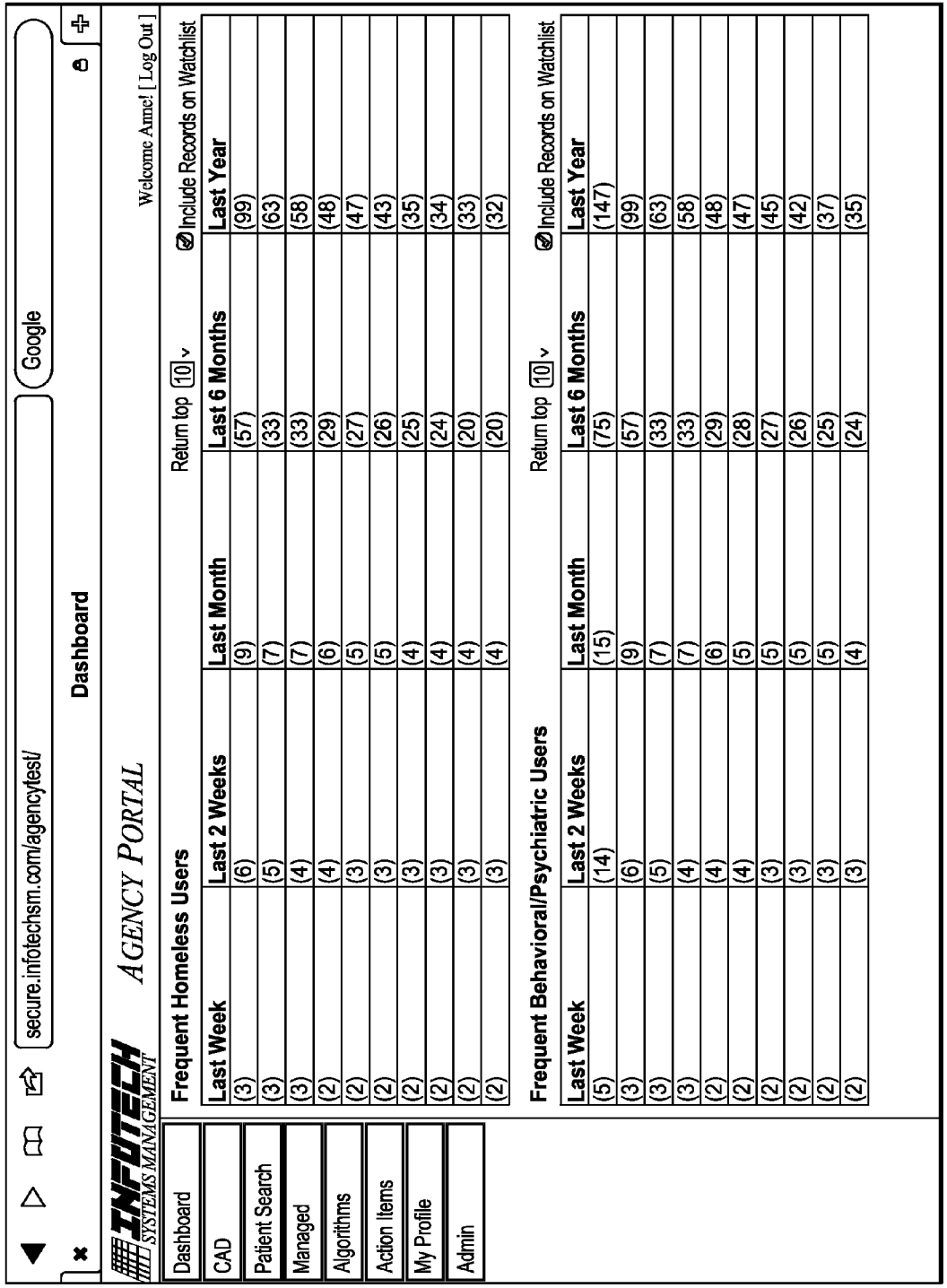
FIG. 16 is a screenshot of vulnerability-specific top user list according to at least one embodiment.

FIG. 7B a process flow diagram of another example method of group alerting. The example process flow of FIG. 7B may be implemented in a manner similar to the implementation of FIG. 7A described above. Additionally, the example method of FIG. 7B illustrates patient or incident matching in a group setting that matches patient and/or incidents based on one or more algorithm criteria at block 810. If the algorithm is on alert list as determined at block 820, the illustrated method proceeds to block 830. As the method illustrated in FIG. 7B relates to group alerting with algorithm matching, the determination of whether additional conditions are met at block 850 may further be based on vulnerability algorithms or matching probability. In one embodiment, when an individual in question meets certain conditions, alerts may be requested based on category of events or individuals who enter a category. A situational alert based on historical data or vulnerability predictions based on the medical report can be set up, such as, an alert for any person in the city who has chest pain related to alcohol consumption five times within a zip code. Or, as another example, any Veteran who, is associated with a record indicating a previous transport to a Veterans Affairs (VA) hospital, but is now asking to be transported to a non-VA hospital for a low-acuity traumatic injury. Such a situation may generate a specialized alert to one or more responders or service providers via a preferred communication channel (e.g., text message, email, telephone call) with the information appropriate to the responder or service provider. It should be appreciated that once a need for an alert is identified, the content of alerts transmitted may differ based on the recipient. For example, if an alert for the Veteran is being sent to a doctor and a VA specialist, the doctor may receive vitals, medical history, or similar health related information pertinent to treating the chief complaint. The VA specialist may receive additional or alternate information perhaps related to the Veteran's service, any Veteran support communities the individual belongs to, or similar service oriented information for the individual.

By way of further example, the system implementing the illustrated process of FIG. 7B may receive a 9-1-1 call corresponding to the 9-1-1 incident at block 800. At block 810, the system determines, based on the location of the call, the phone number, and the age of the caller, that the incident fits an algorithm criteria for a nursing home emergency. At block 820, the system may determine that a nursing home emergency algorithm may set to trigger an alert to report to local authorities if the emergency is determined to be due to poor security, for example. The system at blocks 830 and 850 may determine that this particular place of the call has a known vulnerability of having a low level of security and letting patients leave the vicinity without permission at night. As the system determines this call is based on one of those low-security nursing home incidents, the system may deploy alert as illustrated in block 840.

While the location may be adequate to make some determination of the patient or his condition, the described features also contemplate inclusion of one or more reports (e.g., patient care report, incident report) in matching, categorizing, and alerting for a patient. In such an example, the system may incorporate components of the patient care report in implementing the process of FIG. 7B.

FIG. 8 illustrates a screenshot, according to some embodiments, of a live Computer-Aided Dispatch ("CAD") interface with real-time patient identification. When field responders begin documentation for medical aid, the information is wirelessly pushed to a server, where it may be matched with CAD information. This allows a dispatcher, administrator, or other professional to view 9-1-1 calls that are currently active, know the identity of the individuals, and provide a non-traditional intervention if indicated. Flags and exclamation points may indicate the presence of a vulnerability, high rank, or manual flag for other purposes.

The systems or methods may prioritize special-interest patients. The prioritization may be used to help responders understand overall emergency service usage and efficiently intervene. For example, the patients may be prioritized based on cumulative positions in rank over different time intervals, as well as algorithmic categories. The rank can be determined based on, for example, frequency of 9-1-1 calls or total minutes spent by first responder units. The rank can also be based on machine learning techniques, for example.

The following list of 28 items identifies one example of prioritization levels which may be assigned in an implementation of the described features. One non-limiting advantage of the example prioritization disclosed below is that the system takes into consideration frequency and informal time series observations. The following begins with the highest priority and decreases thereafter:

1. Patient is ranked highly for the week, month, 6 month period and year;
2. Patient is ranked highly for the week and year;
3. Patient has 1 or more 9-1-1 calls for the week, and is ranked highly for the month and year;
4. Patient has 1 or more 9-1-1 calls for the week, and is ranked highly for the year;
5. Patient is ranked highly for the week and top 6 months;

6. Patient has 1 or more 9-1-1 calls and is ranked highly for the month and 6 month period;
7. Patient has 1 or more 9-1-1 calls and is ranked highly for the 6 month period;
8. Patient has 1 or more 9-1-1 calls and has history ranking highly for the year, during the past 3 years;
9. Patient is ranked highly for the week and the month, has more than 5 different incident addresses;
10. Patient is ranked highly for the week and month, is homeless, has a behavioral classification, and has a chronic respiratory classification;
11. Patient is ranked highly for the week and month, is homeless, has a behavioral classification, and has a chronic chest pain classification;
12. Patient is ranked highly for the week and month, is homeless, has a behavioral classification, has a history of respiratory or chest pain incidents;
13. Patient is ranked highly for the week and month, is homeless, majority of calls are alcohol related;
14. Patient is ranked highly for the week and month, is homeless, majority of calls are a combination of alcohol-related and OTHER (no specific chief complaint or primary impression);
15. Patient ranks highly for the week and month, has a behavioral classification, has a chronic respiratory classification;
16. Patient is ranked highly for the week and month, has behavioral classification, has a chronic chest pain classification;
17. Patient ranks highly for the week and month, has a behavioral classification, has a history of respiratory and chest pain incidents;
18. Patient ranks highly for the week and month, majority of calls are a combination of alcohol-related and OTHER (no specific chief complaint or primary impression);
19. Patient ranks highly for the week and has more than 2 different incident addresses;
20. Patient ranks highly for the week, is homeless, majority of calls are alcohol related;
21. Patient ranks highly for the week, is homeless, majority of calls are a combination of alcohol-related and OTHER (no specific chief complaint or primary impression);
22. Patient ranks highly for the week, is homeless, has a behavioral classification, has a chronic chest pain classification;
23. Patient ranks highly for the week, is homeless, has a behavioral classification, has a chronic chest pain classification;
24. Patient ranks highly for the week, is homeless, has a behavioral classification, has a history of respiratory and chest pain incidents;
25. Patient ranks highly for the week, is homeless, calls are either alcohol-related or OTHER (no specific chief complaint or primary impression);
26. Patient ranks highly for the week and month;
27. Patient ranks highly for the week and has more than 1 9-1-1 call in a 24-hour period; and
28. Patient ranks highly for the week.

According to the present disclosure, any number of systems or methods may be used to handle any number of situations or categories of situations. Categories of situations may be developed to aid emergency personnel in handling various situations according to predetermined protocol or procedures. Such categories can include Behavioral/Psychiatric, Chronic Alcoholic, Homeless, Congestive Heart Failure, Stroke, In-home difficulty/Elderly, Seizure, Diabetes, Suicide Attempts, Drug Seeking, Chronic Respiratory, Threat to safety/Homicidal behavior, High Utilizing Family/Household, Skilled nursing 9-1-1 overuse, Pneumonia, Pediatric, Veteran, Drug Seeking behavior, Chronic Pain, Myocardial Infarction, New frequent user identification, and Drug Abuse. According to some embodiments, only a single category may be used in any given incident or combinations of categories may be used. In other embodiments, some categories may negate another, or be dependent on another.

FIGS. 9-16 illustrate various screenshots of a system configured to implement the various process, algorithms, and methods disclosed herein.

EXAMPLE 1

An example process for categorizing congestive heart failure is as described below.

Example Data fields from the incident report which may be used in this example may be compatible with industry standard data structure as below:
1. NEMSIS eDispatch.01—Complaint Reported by Dispatch
2. NEMSIS eSituation.09—Primary Symptom
3. NEMSIS eSituation.10—Other Associated Symptoms
4. NEMSIS eSituation.11—Provider's Primary Impression
5. NEMSIS eSituation.12—Provider's Secondary Impressions
6. NEMSIS eHistory.01—Barriers to Patient Care
7. NEMSIS eHistory.06—Medication Allergies
8. NEMSIS eHistory.08—Medical/Surgical History
9. NEMSIS eHistory.12—Current Medications
10. NEMSIS eMedications.03—Medication Given
11. NEMSIS eSituation.04—Complaint
12. NEMSIS eNarrative
13. NEMSIS eExam.08—Chest/Lungs Assessment
14. NEMSIS eVitals.06—SBP (Systolic Blood Pressure)
15. NEMSIS eVitals.24—Temperature
16. NEMSIS eVitals.25—Temperature Method Example criteria which may be used to classify the incident as a CHF-related incident:
1. "Complaint" is congestive heart failure
2. "Provider's Primary Impression" is heart failure
3. "Provider's Primary Impression" is acute pulmonary edema+"Medical/Surgical History" indicates congestive heart failure
4. "Complaint" is respiratory distress, dyspnea or shortness of breath+"Chest/Lungs Assessment" indicates rales+"Medication Given" is a medication used to treat congestive heart failure (not including nitroglycerin)
5. "Complaint" is respiratory distress, dyspnea or shortness of breath+"Chest/Lungs Assessment" indicates rales+"Medication Given" is nitroglycerin
6. "Complaint" is respiratory distress, dyspnea or shortness of breath+"Chest/Lungs Assessment" indicates rales+"Medical/Surgical History" indicates congestive heart failure
7. "Complaint" is respiratory distress, dyspnea or shortness of breath+"Chest/Lungs Assessment" indicates rales+"Current Medications" include congestive heart failure prescriptions
8. "Complaint" is respiratory distress, dyspnea or shortness of breath+"Chest/Lungs Assessment" indicates rales+narrative includes words or abbreviations associated with dialysis
9. "Complaint" is respiratory distress, dyspnea or shortness of breath+"Chest/Lungs Assessment" indicates rales+Systolic Blood Pressure is less than 90+"Temperature Method" is Axillary, Esophageal, Oral or Rectal+"Temperature" is not greater than 98.6
10. "Complaint" is respiratory distress, dyspnea or shortness of breath+"Chest/Lungs Assessment" indicates rales+Systolic Blood Pressure is less than 90+"Temperature Method" is tympanic+"Temperature" is not greater than 97.6
11. "Complaint" is respiratory distress, dyspnea or shortness of breath+"Chest/Lungs Assessment" indicates wheezes+ Patient age is greater than 65+"Medical/Surgical History" indicates no history of asthma+Systolic Blood Pressure is greater than 150+"Medication Given" is not epinephrine, albuterol or atrovent
12. "Complaint" is chest pain+"Medication Given" is a medication used to treat congestive heart failure (not including nitroglycerin)+"Chest/Lungs Assessment" indicates rales+"Providers Primary Impression" is not STEMI, angina or cardiac related (ICD-10-CM Codes 120.0-149.9)
13. "Complaint" is chest pain+"Medication Given" is nitroglycerin+"Chest/Lungs Assessment" indicates rales+ "Medical/Surgical History" indicates congestive heart failure+"Providers Primary Impression" is not STEMI, angina or cardiac related (ICD-10-CM Codes 120.0-149.9)
14. "Complaint" is chest pain+"Medication Given" is nitroglycerin+"Chest/Lungs Assessment" indicates rales+ "Current Medications" include congestive heart failure prescriptions+"Providers Primary Impression" is not STEMI, angina or cardiac related (ICD-10-CM Codes 120.0-149.9)
15. "Complaint" is chest pain+narrative includes words or abbreviations associated with dialysis+"Chest/Lungs Assessment" indicates rales.

Figure 17:
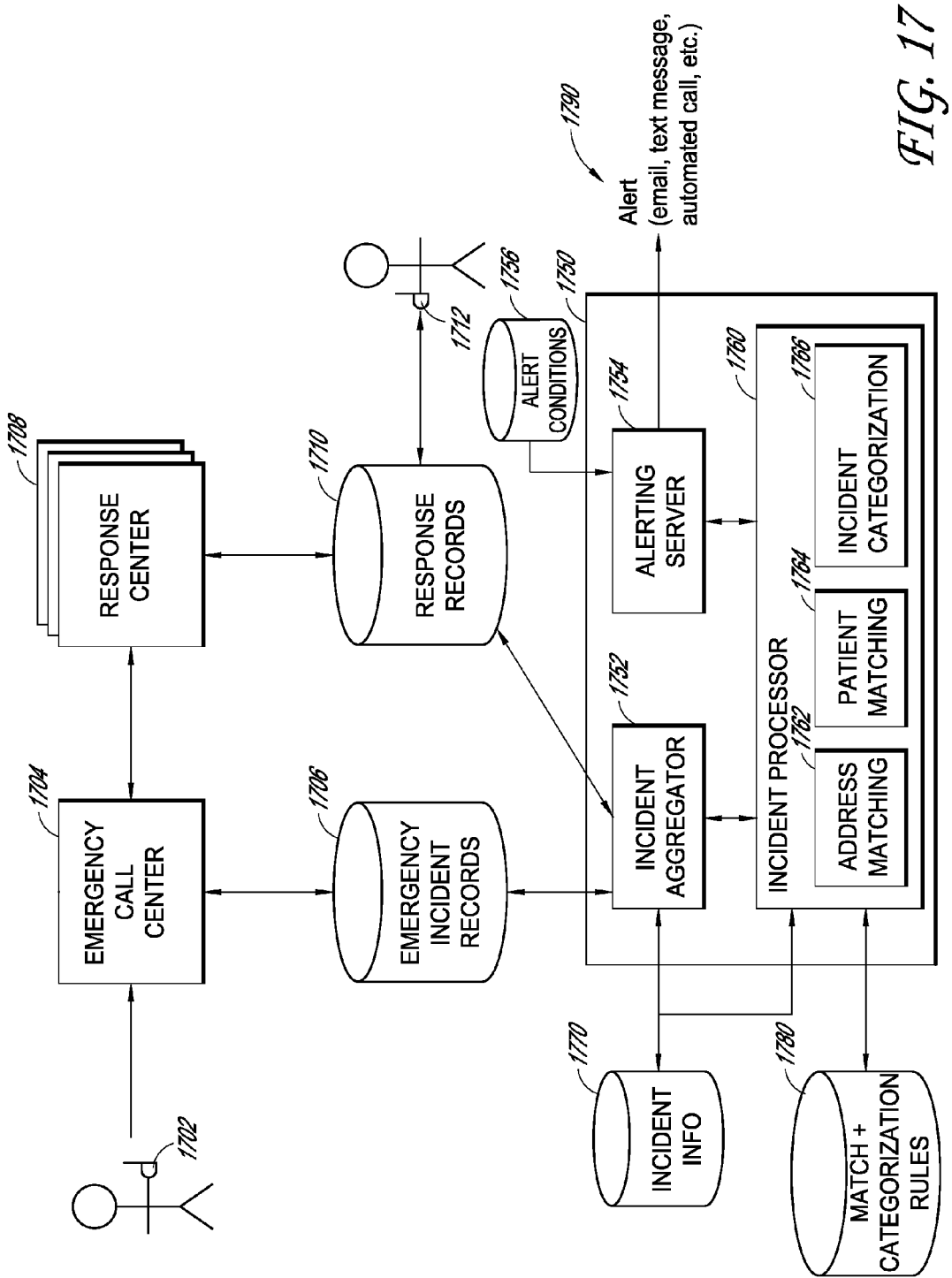
FIG. 17 illustrates a function block diagram for a device configured to provide assistance for repeat users of an emergency service.

FIG. 17 illustrates a function block diagram for a device configured to provide assistance for repeat users of an emergency service. The device 1750 is shown in a context of an emergency response system. As one example of how the system may operate, an emergency call may be received from a communication device 1702. The communication device 1702 shown in FIG. 17 is a handheld wireless device; however other communication devices may be used to transmit an emergency call. The communication device 1702 may be a cellular telephone, mobile telephone, smart phone, land line telephone, laptop computer, tablet computer, desktop computer, video recording device, or other electronic communication device configured to transmit information via wired and/or wireless means.

The communication device 1702 transmits the emergency call to an emergency call center 1704. The emergency call center 1704 is configured to receive the emergency call information and further process the emergency situation so as to cause an appropriate response thereto. For example the emergency call center 1704 may include operators who interact with the emergency caller to obtain the necessary incident information to respond to the emergency. The information regarding the emergency call may be stored in an emergency incident records database 1706.

The emergency call center 1704 may identify an appropriate response for the emergency incident. The identification may be based on the information obtained during the emergency call. For example, if the call information indicates a fire is burning, a message may be sent from the emergency call center 1704 to a response center 1708. In the example where a fire is involved, the response center 1708 may be a fire dispatch. As shown in FIG. 17, the emergency call center 1704 may transmit messages to more than one response center for a given emergency incident. A response center may record information regarding the incident and their response thereto in and in response records database 1710.

The response records database 1710 may also receive information from a wireless communication device 1712 associated with an emergency responder. The response records database 1710 may further store instructions for bidirectional feedback to responders, and such feedback may be generated using additional processors (not shown) associated with the database. For example, an emergency medical technician may use a laptop computer to transmit information regarding an incident they are responding to. The device 1712 may be a cellular telephone, mobile telephone, smart phone, land line telephone, laptop computer, tablet computer, desktop computer, video recording device, or other electronic communication device configured to transmit information via wired and/or wireless means.

It will be noted that as shown in FIG. 17, the emergency call center 1704 and the response center 1708 communicate bidirectionally. As information is exchanged regarding an incident, the corresponding records in the emergency incident records database 1706 and/or response records database 1710 may be updated. In some implementations, and incident identifier may be assigned to an emergency call and used to reference the incident during the process.

The device 1750 includes an incident aggregator 1752. The incident aggregator 1752 is configured to obtain the emergency incident record information and emergence the response record information from the emergency incident records database 1706 and the response records database 1710, respectively. In some implementations, the incident aggregator 1752 may obtain the incident information and/or response information directly from the emergency call center 1704 and/or the response center 1708. Information received may be stored in an incident information database 1770. The incident information database 1770 is shown to be outside the device 1750. In some implementations, the device 1750 may include the incident information database 1770.

The aggregated incident information may be provided to an incident processor 1760 such as a matching engine. The incident processor 1760 may include an address matching module 1762, a patient matching module 1764, and/or an incident categorization module 1766. These modules may be configured to perform the categorization described above.

As the incident processor 1760 performs various matching and categorization foreign incident, the processed information may be transmitted for storage in the incident information database. The incident processor 1760 may also be in data communication with a match and categorization rules database 1780. The match and categorization rules database 1780 may be used to store the criteria upon which matching may be performed. The matching and categorization rules database 1780 may also store the categories and vulnerabilities as well as the criteria associated therewith for incident categorization. The device 1750 may provide an interface to create and update match and categorization rules stored in the match and categorization rules database 1780. The match and categorization rules database 1780 may further be configured to accept manual and/or programmable inputs from the user such as emergency respondents or experts to reflect changes in rules and priorities based on the user's experience. Therefore, the matching and categorization rules database 1780 may be updated periodically or aperiodically for faster matching, for example. The incident processor 1760 may include a predictor engine (not shown) configured to generate prediction results based on data from the incident aggregator 1752. The predictor engine may determine the likelihood of an individual becoming a high frequency user of the emergency call system.

The device 1750 also includes an alerting server 1754. The alerting server 1754 may be configured to generate and transmit alerts such as described in reference to FIG. 7. The alerting server 1754 may consult an alert conditions database 1756 which includes the conditions, upon which an alert may be transmitted, communication channel to be used for the transmission, contact information for the alert destinations, and the like. The alerting server 1754 may generate an alert 1790. The alert 1790 may be an email, text message, an automated call, and the like. For a given incident, more than one alert may be generated.

FIG. 17 includes three databases in data communication with the device, namely the alert conditions database 1756, the incident information database 1770, and the matching categorization rules database 1780. Although shown a separate data storages, a common database may be used to combine the information stored in two or more of the described databases.

Many examples provided above relate to emergency services. However, it will be understood that the concepts of categorizing incidence data may be implemented in a range of organizational settings. For instance, a business determining how to improve its safety record may benefit from the aspects described above in analyzing the type and nature of past incidents to determine how to best handle future incidents. Businesses may utilize the systems and methods described to provide information to employees. Furthermore, medical organizations such as a doctor's practice, a practice group, a hospital, a managed care facility, rehabilitation center, or other health care organization may implement one or more aspects described. These are merely provided as examples and other implementations for different organizations are contemplated.

In one innovative aspect, a method for assisting repeat users of an emergency service is provided. The method includes receiving an electronic report for an incident or individual, matching a person identifier from the electronic report with person-centric data from a database, wherein the matching comprises identifying if the individual matches a list of frequent or high priority emergency service users and if so, then providing an alert to a specialized caregiver.

In some implementations, the electronic report may include a checklist or notes from a firefighter, peace officer, paramedic, or health care professional.

In some implementations, the electronic report comprises a medical history of a list of current medications.

In some implementations, the person identifier includes at least one of a social condition, a medical condition, or a type of medical complaint. The social condition may indicate a vulnerability for the individual or incident. The condition or vulnerability may be determined by medical or demographic information in the electronic report.

In some implementations, the method also includes classifying the vulnerability, social condition, medical condition or medical compliant as at least one of a stroke, drug seeking behavior, chronic pain, chronic alcoholic, diabetic problem, psychiatric symptom, myocardial infarction, or congestive heart failure. The classifying may also be based on keywords in notes form a patient care report.

In some implementations, the person identifier includes patient name, social security number, location of emergency call, or history of transport.

The database may include one or more of a fire department database, police department database, emergency medical services database, other first-responder database, hospital database, emergency call ("911") database, city or county government database, state government or agency database, or federal government or agency database.

The specialized caregiver may include a social worker, a case manager, a nurse, a paramedic, a counselor, or a doctor.

In some implementations, providing an alert comprises a text message, an email or a page.

The method in some implementations includes generating a risk level based on the electronic report, the risk level indicating hazardous conditions for the individual and/or the specialized caregiver. The risk level may be generated based on an individual identified in the electronic report. The individual may be associated with one or more previous incidents. In may be desirable for the risk level to be generated based on a location associated with the electronic report.

In some implementations, providing the alert comprises obtaining previously provided alerts, determining a priority for the alert based on the previously provided alerts or information, and providing the alert including the priority.

In another innovative aspect, an emergency service device is provided. The device includes a receiver configured to receive an electronic report for an incident or individual. The device includes an incident processor configured to match a person identifier from the electronic report with person-centric data from a database, the matching including identifying if the person matches a list of frequent or high priority emergency service users. The device further includes an alert transmitter configured to generate an alert for transmission to a specialized caregiver based on the identified individual.

In yet another innovative aspect, a non-transitory computer-readable medium comprising instructions executable by a processor of a device is provided. The instructions cause the device to receive an electronic report for an individual. The instructions cause the device to match a person identifier from the electronic report with person-centric data from a database, wherein the matching comprises identifying if the individual matches a list of frequent or high priority emergency service users. The instruction further cause the device to generate an alert for transmission to a specialized caregiver based on the identified individual.

In the detailed description, only certain exemplary embodiments have been shown and described, simply by way of illustration. As those skilled in the art would realize, the described embodiments may be modified in various different ways, all without departing from the spirit or scope of the present disclosure. Accordingly, the drawings and description are to be regarded as illustrative in nature and not restrictive. In addition, when an element is referred to as being "on" another element, it can be directly on another element or be indirectly on another element with one or more intervening elements interposed there between. Also, when an element is referred to as being "connected to" another element, it can be directly connected to another element or be indirectly connected to another element with one or more intervening elements interposed there between. Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

The detailed description set forth in connection with the appended drawings is intended as a description of exemplary embodiments and is not intended to represent the only embodiments in which the invention may be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments. It will be apparent that the exemplary embodiments may be practiced without these specific details. In some instances, some devices are shown in block diagram form.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. As used herein, the term "and/or" includes any and all combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

As used herein, the term "determining" encompasses a wide variety of actions. For example, "determining" may include calculating, computing, processing, deriving, investigating, looking up (for example, looking up in a table, a database or another data structure), ascertaining and the like. Also, "determining" may include receiving (for example, receiving information), accessing (for example, accessing data in a memory) and the like. Also, "determining" may include resolving, selecting, choosing, establishing and the like.

As used herein, the terms "provide" or "providing" encompass a wide variety of actions. For example, "providing" may include storing a value in a location for subsequent retrieval, transmitting a value directly to the recipient, transmitting or storing a reference to a value, and the like, or a combination thereof. "Providing" may also include encoding, decoding, encrypting, decrypting, validating, verifying, and the like.

As used herein, the terms "obtain" or "obtaining" encompass a wide variety of actions. For example, "obtaining" may include retrieving, calculating, receiving, requesting, and the like, or a combination thereof. Data obtained may be received automatically or based on manual entry of information. Obtaining may be through an interface such as a graphical user interface.

As used herein a graphical user interface may include a web-based interface including data fields for receiving input signals or providing electronic information. The graphical user interface may be implemented in whole or in part using technologies such as HTML, Flash, Java, .net, web services, and RSS. In some implementations, the graphical user interface may be included in a stand-alone client (for example, thick client, fat client) configured to communicate in accordance with one or more of the aspects described.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

Information and signals may be represented using any of a variety of different technologies and techniques. For example, data, instructions, commands, information, signals, bits, symbols, and chips that may be referenced throughout the above description may be represented by voltages, currents, electromagnetic waves, electromagnetic fields or particles, optical fields or particles, or any combination thereof.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the embodiments of the disclosure.

The various illustrative blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any processor, controller, microcontroller, or state machine. A processor may also be implemented as a combination of computing devices, for example, a combination of a DSP and a microprocessor or a plurality of microprocessors, in conjunction with a DSP core, or any other such configuration.

The steps of a method or algorithm and functions described in connection with the embodiments disclosed herein may be embodied directly in hardware, in a software module executed by a processor, or in a combination of the two. If implemented in software, the functions may be stored on or transmitted over as an instruction, instructions or code on a tangible, non-transitory computer-readable medium. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art. A storage medium is coupled to the processor such that the processor can read information from, and write information to, the storage medium. In the alternative, the storage medium may be integral to the processor. Disk and disc, as used herein, includes compact disc (CD), laser disc, optical disc, digital versatile disc (DVD), floppy disk and blu ray disc where disks usually reproduce data magnetically, while discs reproduce data optically with lasers. Combinations of the above should also be included within the scope of computer readable media. The processor and the storage medium may reside in an ASIC. The ASIC may reside in a user terminal. In the alternative, the processor and the storage medium may reside as discrete components in a user terminal.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

For purposes of summarizing the disclosure, certain aspects, advantages and novel features have been described herein. It is to be understood that not necessarily all such advantages may be achieved in accordance with any particular embodiment. Thus, the invention may be embodied or carried out in a manner that achieves or optimizes one advantage or group of advantages as taught herein without necessarily achieving other advantages as may be taught or suggested herein.

While this invention has been described in connection with what is are presently considered to be practical embodiments, it will be appreciated by those skilled in the art that various modifications and changes may be made without departing from the scope of the present disclosure. It will also be appreciated by those of skill in the art that parts mixed with one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. Thus, while the present disclosure has described certain exemplary embodiments, it is to be understood that the invention is not limited to the disclosed embodiments, but, on the contrary, is intended to cover various modifications and equivalent arrangements included within the scope of the appended claims, and equivalents thereof.

What is claimed is:

1. A method for emergency service contact alerting, the method comprising:
   receiving an electronic report input associated with an incident or individual;
   obtaining a rule for matching from a matching and categorization rules storage, wherein the rule identifies one or more characteristics for an incident or an individual and a match priority;
   categorizing the electronic report input with a matching engine and a database based on a person identifier and a comparison of values included in the electronic report input for characteristics identified via the rule with values included in previously received electronic report inputs, the matching engine configured to assign one or more categorization attributes of the incident or individual;
   generating a response risk level for the electronic report input, the response risk level being based on one or more hazardous conditions identified for a user of a specialized caregiver device responding, the one or more hazardous conditions being associated with the incident, the individual, or the person identifier; and
   generating an alert provision instruction to one or more specialized caregiver devices based on the one or more categorization attributes and an alert condition, wherein the alert condition identifies a value included in the electronic report input and an indicator identifying whether or not an alert should be sent to specific specialized caregiver devices when the value is included in the electronic report input.

2. The method of claim 1, wherein an electronic report input comprises a checklist or notes from a firefighter, peace officer, paramedic, or health care professional.

3. The method of claim 1, wherein the electronic report input comprises a medical history of a list of current medications.

4. The method of claim 1, wherein the person identifier comprises a social or medical condition, or another type of medical complaint.

5. The method of claim 1, wherein the matching engine is further configured to assign the one or more categorization attributes based on one or more vulnerability factor values, wherein the one or more vulnerability factor values are determined by medical or demographic information in the electronic report input.

6. The method of claim 5, wherein the one or more vulnerability factor values are further determined by as at least one condition indicated in the electronic report input, such as stroke, drug seeking behavior, chronic pain, chronic alcoholic, diabetic problem, psychiatric symptom, myocardial infarction, or congestive heart failure.

7. The method of claim 6, wherein the one or more vulnerability factor values are classified based a chief complaint input, wherein the chief complaint input comprises one or more keywords in notes form a patient care report.

8. The method of claim 1, wherein the person identifier comprises location of a prior emergency call, or history of transport.

9. The method of claim 1, wherein the database comprises a fire department database, police department database, emergency medical services database, other first-responder database, hospital database, emergency call ("911") database, city or county government database, state government or agency database, or federal government or agency database.

10. The method of claim 1, wherein the one or more specialized caregiver devices comprises one or more assigned devices of a social worker, a case manager, a nurse, a paramedic, a counselor, or a doctor.

11. The method of claim 1, wherein the alert provision instruction comprises an electronic instruction for providing an alert through a text message, an email, or a page.

12. The method of claim 1, wherein the risk level is generated based on an individual identified in the electronic report input.

13. The method of claim 12, wherein the individual is associated with one or more previous incidents.

14. The method of claim 1, wherein the risk level is generated based on a location associated with the electronic report input.

15. The method of claim 1, wherein generating an alert provision instruction comprises:
   obtaining at least one previously provided alert or associated information;
   determining a priority for the alert provision instruction based on the obtained previously provided alert or the associated information; and
   generating an alert provision instruction including the priority.

16. An emergency service device, comprising:
   a receiver configured to receive an electronic report input associated with an incident or individual;
   an incident processor configured to:
      obtain a rule for matching from a matching and categorization rules storage, wherein the rule identifies one or more characteristics for an incident or an individual and a match priority,
      match a person identifier from the electronic report input with person-centric data from a database based on a comparison of values included in the electronic report input for characteristics identified via the rule with values included in previously received electronic report inputs, the matching comprising assigning one or more categorization attributes corresponding to frequency or priority of the incident or individual, and
generate a response risk level for the electronic report input, the response risk level being based on one or more hazardous conditions identified for a user of a specialized caregiver device responding, the one or more hazardous conditions being associated with the incident, the individual, or the person identifier; and an alert transmitter configured to generate an alert for transmission to one or more specialized caregiver devices based on the matched individual and an alert condition, wherein the alert condition identifies a value included in the electronic report input and an indicator identifying whether or not an alert should be sent to specific specialized caregiver devices when the value is included in the electronic report input.

17. The emergency service device of claim 16, wherein the receiver is configured to wirelessly communicate with an emergency incident storage device and an emergency response center response storage device, wherein the receiver is configured to receive the electronic report input of an incident from the emergency incident storage device, and wherein the receiver is configured to receive the electronic report input for an individual from at least one of the emergency incident storage device and the emergency response center response storage device.

18. The emergency service device of claim 16, wherein the incident processor is configured to match the person identifier with person-centric data using a history of transports from a location.

* * * * *